United States Patent [19]

Moore

[11] Plant 4,070

[45] July 5, 1977

[54] ROSE PLANT

[76] Inventor: Ralph S. Moore, 2519 E. Noble Ave., Visalia, Calif. 93277

[21] Appl. No.: 719,607

[22] Filed: Sept. 1, 1976

[51] Int. Cl.[2] ..... A01H 5/00

[52] U.S. Cl. ..... Plt./9

[58] Field of Search ..... Plt./9

*Primary Examiner*—Robert E. Bagwill

[57] ABSTRACT

This invention relates to a novel miniature rose variety characterized by its lavender blossoms which are similar to Angel Face.

1 Drawing Figure

1

The present invention relates to a new and distinct variety of hardy, dwarf, bush type rose plant of the miniature class; the variety being primarily characterized — as to novelty — by buds and flowers of a lavender (mauve) shade which in general color effect are similar to Angel Face (Floribunda — U.S. Plant Pat. No. 2,792).

The variety is further characterized by:

An abundance of bloom with flowers borne singly or several to stem in loose small clusters.

Sweet fragrance.

A plant which is vigorous, of rounded spreading shape and with semi-glossy, medium-small foliage with pointed leaflets; the buds and flowers being similar in form to New Penny, miniature (not patented), but of somewhat larger size.

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Little Chief (miniature — not patented) as the seed parent and Angel Face (Floribunda — U.S. Plant Pat. No. 2,792) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers. Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; seedling; greenhouse; outdoors; cut flowers; garden decoration; potted plant.

Class: Miniature. Variety name: 'Angel Darling'.

Flowers: Continuity; continuous — repeat bloom all season. Fragrance; sweet.

Flowers borne; Singly and several together (three to five) on sturdy, wirey, medium length stems.

Quantity of bloom: Abundant both outside and in greenhouse.

Bud: Peduncle — medium length; slender but sturdy;

2 erect; medium green, sometimes tinted bronze (outdoors); hairs — unusually smooth — no hairs, no prickles. Before calyx breaks; size — small. Form: long; pointed with few foliaceous appendages and few or no hairs on surface of bud; with foliaceous parts extending beyond the tip of the bud equal to one-half or less of its length. Color — medium green, occasionally tinted with bronze (outdoors). As calyx breaks, color — lavender or pinkish lavender (sometimes with brownish cast); opens: same general color or lighter shade. Size — small.

Bloom: Size when fully open — small, averaging about 35 to 45 mm. Petalage — semi-double — usually about 11 petals, arranged regularly. Form — open; shows yellow stamens on fresh flowers, with petals often loosely waved.

Petals: Thick; satiny on inside and on outside surface. Shape — outside petals, broad lanceolate, being almost round with very small acute tip; intermediate and/or inside — broad lanceolate nearly round with very small acute tip.

Color: Newly opened flower from a plant grown in plastic greenhouse (August, 1976), Visalia, Calif.

*Outside petal.*—Outside surface — near Rosine Purple 629/1 with both lighter and darker areas, and with small near white or yellowish area at base; inside surface — near Rosine Purple 629/2 or lighter, shading into near white at base.

*Inner petal.*—Outside surface — same as outside petal; inside surface — same as outside petal. General color effect newly opened flowers — medium shade of lavender or pinkish lavender (sometimes with grayish or chocolatey undertone. Three days open — color similar to newly opened flowers but lighter shade. Behavior — as flowers age color may become more pink; flower color holds extremely well even in summer heat. Spent petals drop off. Flower longevity (July, 1975) — plant in pot 3–5 days or longer; outdoors in ground — 4–6 days or longer. Cut flowers at living room temperature 3–4 days.

Reproductive Organs:

*Stamens.*—Abundant, arranged regularly about pistil.

*Filaments.*—Varying length, light yellow, short to medium.

*Anthers.*—Well formed; yellow.

*Pollen.*—Fair amount to abundant.

*Pistils.*—Average number.

*Styles.*—Fairly uneven; short to medium length; bunched; color — pinkish.

*Stigma.*—Pinkish.

*Ovaries.*—All enclosed in calyx.

*Hips.*—Few or none.

*Sepals.*—Permanent; spear shaped; recurved.

*Seed.*—Few or none.

Foliage:

*Leaves.*—Compound of five (sometimes three or seven) leaflets; abundant; medium small; leathery; semi-glossy.

*Leaflets.*—Shape: broad lanceolate; apex acute; base rounded or rounded acute. Margin serrate. Color: medium green; new growth — reddish or bronze. Rachis: medium strength; upper side usually smooth with no hairs or prickles, grooved; underside — few or no thorns or prickles. Stipules: medium long; narrow to medium width medium length narrow points which turn out usually at 45° or more.

Growth:

*Habit.*—Dwarf; bushy; spreading; much branched.

*Growth.*—Free vigorous.

*Canes.*—Medium; slender; sturdy.

*Main stems.*—Color; medium green.

*Thorns.*—Few; usually small; curved; hooked downward; color; brown. Prickles — none. Hairs — none.

*Branches.*—Color: medium green. Thorns: few; short length; slender; hooked downward. Medium to short oval base. Prickles: none. Hairs: none.

*New shoots.*—Color: often tinted reddish or bronze. Thorns: few; color; reddish; hooked. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, spreading, much branched habit, essentially as illustrated and described, characterized by buds and flowers of a medium lavender or lavender pink color resembling the 'Angel Face' Floribunda rose (U.S. Plant Pat. No. 2,792) and resembling the New Penny miniature rose (not patented) in form of bud and flower — the buds and flowers being somewhat larger in size than New Penny; and further characterized by a plant which is vigorous and compact, said plant being easy to propagate from cuttings, with medium small, disease resistant, semi-glossy, foliage, an abundance of bloom, with flowers borne singly or several to the stem in small clusters.

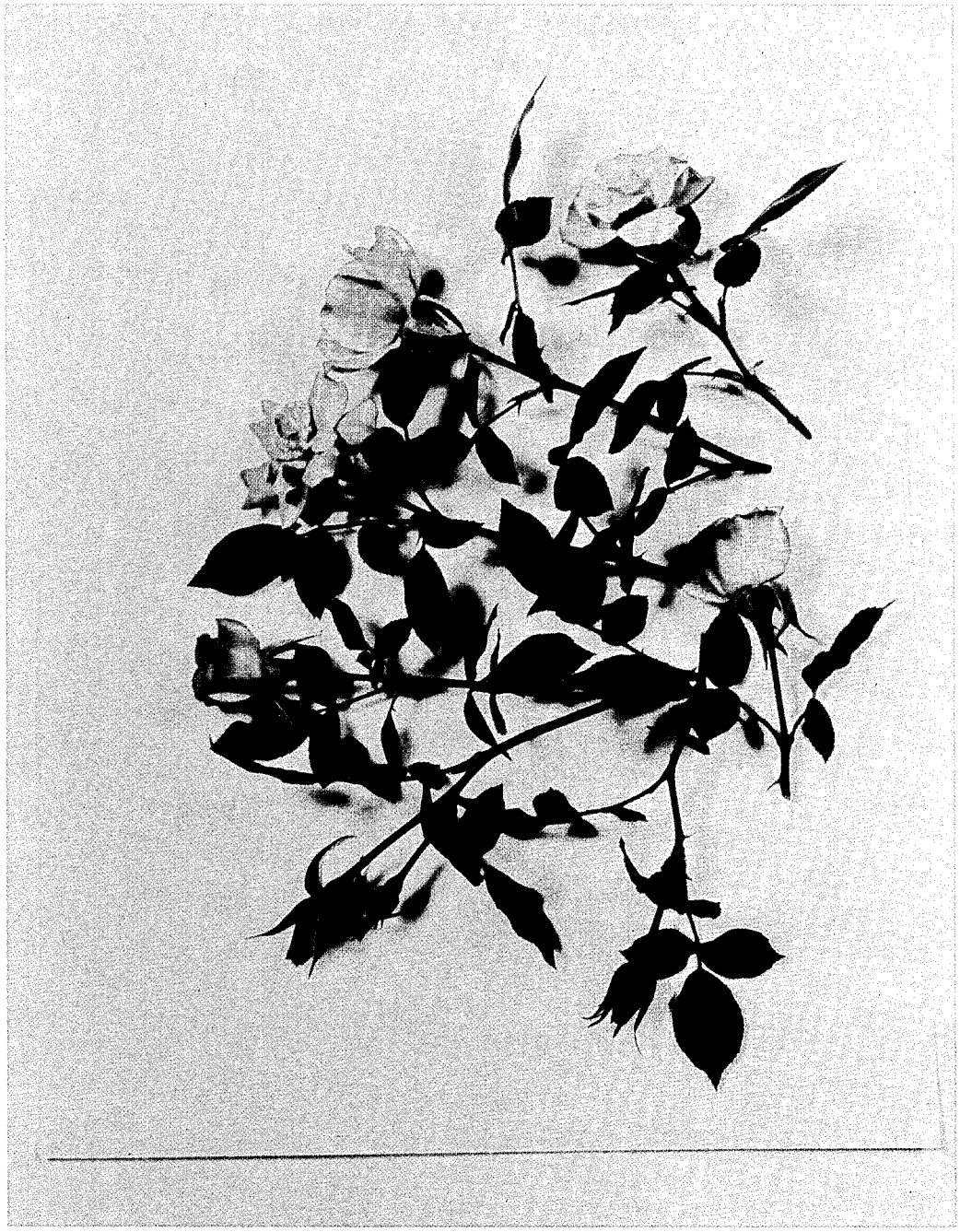

* * * * *